United States Patent [19]

Gustilo et al.

[11] Patent Number: 5,601,564
[45] Date of Patent: Feb. 11, 1997

[54] CANNULATED BROACH FOR TOTAL JOINT ARTHROPLASTY

[75] Inventors: Ramon B. Gustilo, Eden Prairie; Todd J. Hein, Minneapolis, both of Minn.

[73] Assignee: Orthopaedic Innovations, Inc., Minneapolis, Minn.

[21] Appl. No.: 528,063

[22] Filed: Sep. 14, 1995

Related U.S. Application Data

[63] Continuation of Ser. No. 158,603, Nov. 24, 1993, abandoned.

[51] Int. Cl.⁶ .................................................. A61B 17/56
[52] U.S. Cl. .................................................. 606/86; 606/99
[58] Field of Search ............................ 606/84, 85, 92, 606/93, 99, 79, 86

[56] References Cited

U.S. PATENT DOCUMENTS

| | | | |
|---|---|---|---|
| 5,089,004 | 2/1992 | Averill et al. | 606/85 |
| 5,108,405 | 4/1992 | Mikhail et al. | 606/96 |
| 5,147,408 | 9/1992 | Noble et al. | 606/85 |
| 5,180,388 | 1/1993 | DiCarlo | 623/16 |
| 5,192,283 | 3/1993 | Ling et al. | 606/93 |
| 5,197,967 | 3/1993 | Wilson | 606/79 |
| 5,222,955 | 6/1993 | Mikhail | 606/80 |
| 5,234,433 | 8/1993 | Bert et al. | 606/88 |
| 5,312,412 | 5/1994 | Whipple | 606/105 |
| 5,324,293 | 6/1994 | Rehmann | 606/85 |

*Primary Examiner*—Michael Powell Buiz
*Assistant Examiner*—Mark S. Leonardo
*Attorney, Agent, or Firm*—Gregory F. Cotterell

[57] ABSTRACT

A method of preparing an intermedullary canal of a bone for total joint arthroplasty including drilling a hole into the intermedullary cavity of a bone and inserting a centering rod longitudinally into the intermedullary canal of the bone. The rod is inserted to align the rod along the longitudinal axis of the bone. Osteotomizing the articulating surface of the bone and preparing the intermedullary canal of the bone to receive a prosthesis. The preparation including placing cannulated instruments in a telescoping manner over the centering rod and into the intermedullary canal to create a cavity suitable for receiving a bone prosthesis. The cannulated instrumentation includes a cannulated osteotomy guide, a cannulated reamer, a cannulated box chisel, and a cannulated broach. The instrumentation is also disclosed.

6 Claims, 6 Drawing Sheets

CANNULATED BROACH FOR TOTAL JOINT ARTHROPLASTY

This is a continuation of prior application Ser. No. 08/158,603, filed Nov. 24, 1993, now abandoned.

FIELD OF THE INVENTION

The present invention relates to replacement or joint arthroplasty. Specifically, the present invention provides a method of preparing an intermedullary canal of a bone for total joint arthroplasty. The invention further relates to instrumentation used in the method of preparation. More specifically, the present invention relates to substantially rigid cannulated instrumentation to prepare an intermedullary canal of a bone for total joint arthroplasty.

BACKGROUND OF THE INVENTION

In the elderly and injured populations, total joint arthroplasty or replacement is often required for a patient to function and ambulate normally. Orthopaedic surgeons have successfully implanted cemented total joint systems into patients. Although these systems have proven successful over long periods, surgeons are constantly attempting to increase the success rate of total joint arthroplasty.

Total joint replacement requires an involved surgical procedure conducted by a trained surgeon. Once the tissue surrounding the wounded joint has been temporarily removed, the surgeon begins preparing the intermedullary canal of a bone for the total joint arthroplasty. In the case of hip arthroplasty, the intermedullary canal of the femur is prepared in the following manner.

The proximal end of the femoral neck is first osteotomized. A gauge or osteotomy template is placed on the femur to provide the surgeon with a reference to decide where to sever the femoral neck. Once the femoral neck is removed, the femoral canal is exposed and is ready to be prepared to accept the femoral component of a total hip prosthesis. A few instruments are used in the procedure. These include a reamer, a broach, and optionally, a box chisel. All of these instruments are commonly known in the art of orthopaedic surgery.

A reamer is first positioned into the femoral intermedullary canal. While inserting the reamer, the surgeon rotates the reamer to sever the tissue and to enlarge the intermedullary canal. When the surgeon feels that enough tissue has severed, the surgeon removes the reamer from the femoral intermedullary canal.

A box chisel is next optionally employed. The box chisel is placed in the cavity created by the reamer. The box chisel is used to prepare the femur for improved broaching and to orient the broach for proper placement and anteversion. The box chisel prepares the opening of the cavity to comply with the cross-sectional geometry of a broach which is substantially rectangular in shape. A mallet or hammer is used to chisel the bone until the box chisel reaches the appropriate depth. The box chisel is then removed.

A broaching instrument, or simply called a broach, is next inserted into the intermedullary canal to create a cavity compatible with the prosthesis geometry. The surgeon must take care to insert the length of the broach along the same axis as was formed by the reamer. The surgeon impacts the protruding surface of the broach with a mallet or slide hammer until the collar of the broach is properly seated on the severed femoral neck surface.

A provisional neck is next placed in the broach to achieve proper neck length of the prosthesis. The provisional neck is adjusted until proper reduction is achieved to allow for proper range of motion in the joint. The provisional neck is then detached and the broach is removed from the intermedullary canal.

Finally, after the preceding preparation is complete, the femur is now ready to accept the femoral stem of a hip prosthesis. The femoral stem is cemented or press-fit into place and is now ready to accept the ball portion of the joint.

In the past, surgeons have employed a flexible wire in the above-described procedure. The wire was inserted into the length of the bone before reaming. The wire served as a guide over which a flexible reamer having a longitudinal bore therein was telescopically placed. Since the wire was flexible, it did not successfully serve as a guide for intermedullary canal preparation because the guide was not stationary. Instruments placed along or over the wire were free to move within the canal as freely as if no guide wire existed. Only flexible instrumentation was used in the prior art procedures which limited the surgeon's ability to effectively prepare the bone for accepting a prosthesis. The bores in the instruments were very small in diameter since the bores only had to fit over a wire having a diameter of up to about 1 millimeter.

When preparing a bone for a prosthesis, surgeons have consistently been met with the problem of locating the central axis of a bone. Location of the central axis of the bone is critical for a successful operation. If the prosthesis is not centered, uneven weight distribution causes problems both with respect to the bone and the prosthesis. Since the entire bone is not exposed during total arthroplasty, the surgeon has only a limited view of a portion of the bone. Therefore, locating the bone's axis is exceedingly difficult. To date, orthopaedic surgeons have not had reliable methods of successfully or accurately locating a bone's central axis.

The above-described procedure is met with other difficulties. If the surgeon does not insert the broach into the same cavity that the reamer was placed, the surgeon may easily crack the patient's bone. This results in prolonged surgery and prolonged healing time. The surgeon must also take care not to create an area which is exceedingly large and therefore is not suited to receive a prosthesis.

The present invention helps to alleviate the above-cited problems inherent in preparing an intermedullary canal of a bone for total joint arthroplasty. The present invention provides a method of preparing the bone and instrumentation used to conduct the method.

SUMMARY OF THE INVENTION

The present invention provides a method of preparing an intermedullary canal of a bone for total joint arthroplasty. The invention further includes instrumentation necessary to conduct the disclosed method.

The method for preparing an intermedullary canal of a bone for total joint arthroplasty is disclosed. The method comprises drilling a hole into the intermedullary cavity of the bone near or at the articulating surface of the bone. A substantially rigid centering rod is inserted into the hole formed by the drill and placed into the intermedullary cavity of the bone until the rod is securely imbedded in the bone. This causes the centering rod to align with the center axis of the bone. This is a simple, nearly fool proof method of finding the center axis of the bone. It also provides a guide by which the surgeon can routinely prepare an intermedullary canal for receiving a prosthesis. An osteotomy template including a cannulated securement device is next inserted over the centering rod. Using the template as a guide, the bone is marked for osteotomization and the articulating surface of the bone is osteotomized to expose the intermedullary canal of the bone. A substantially rigid cannulated reamer is telescopically placed over the centering rod and the intermedullary canal of the bone is reamed to sever the tissue. After reaming is complete, the reamer is removed from the intermedullary canal and from the centering rod. A substantially rigid cannulated broach is next telescopically placed over the centering rod and into the bone canal. The centering rod provides an axis upon which the cannulated orthopaedic instrumentation is placed. The rod ensures that the instrumentation is placed along the same axis throughout the procedure. The centering rod is next removed and a provisional neck is placed into the broach to achieve proper neck length for a trial reduction. Once the provisional neck is adjusted to achieve proper range of motion, the provisional neck and broach are removed from the bone. Completing this procedure, the bone is prepared and ready to accept a prosthesis.

The present invention also provides a substantially rigid centering rod, a substantially rigid cannulated reamer, a substantially rigid cannulated broach, a cannulated box chisel, and a cannulated osteotomy template. The cannulated instruments, when used in accordance with the method of the invention provide a nearly foolproof method of preparing an intermedullary canal of a bone for total joint arthroplasty. The present invention aids the surgeon in preparing a properly sized and placed cavity in the intermedullary canal for successful placement and retention of a prosthesis. The present method and instrumentation offers a surgeon the ability to avoid several typical surgical complications. This helps to reduce the length of the surgery. This is particularly important with elderly patients because it is important to limit the time the patient is anesthetized. Additionally, the procedure reduces the time that an operating room is occupied thus reducing overall health care costs. The present invention also reduces the likelihood of cracking a bone while preparing its intermedullary canal for a prosthesis.

DETAILED DESCRIPTION OF THE INVENTION

The procedures and instrumentation used in the present invention are shown generally in FIGS. 1 through 15. For purposes of description only, a femur is discussed in this detailed description. One skilled in the art will recognize that the procedure and instrumentation of the present invention is equally useful to prepare any intermedullary canal of any bone for receiving a prosthesis.

After making an incision proximal to the joint needing total arthroplasty, the surgeon temporarily removes surrounding tissue from the articulating surfaces of the joint. For purposes of description only, if a total hip arthroplasty is described, the surgeon removes the tissue from the proximal end of the femur and from the acetabulum. After displacing the joint, the surgeon drills a hole into the intermedullary canal of the femur near the articulating surface needing replacement.

A qualified surgeon determines where to drill the entry point by reviewing preoperative x-rays. The decision of the placement of the drill is a technique commonly known in the art by orthopaedic surgeons.

Figure 1:
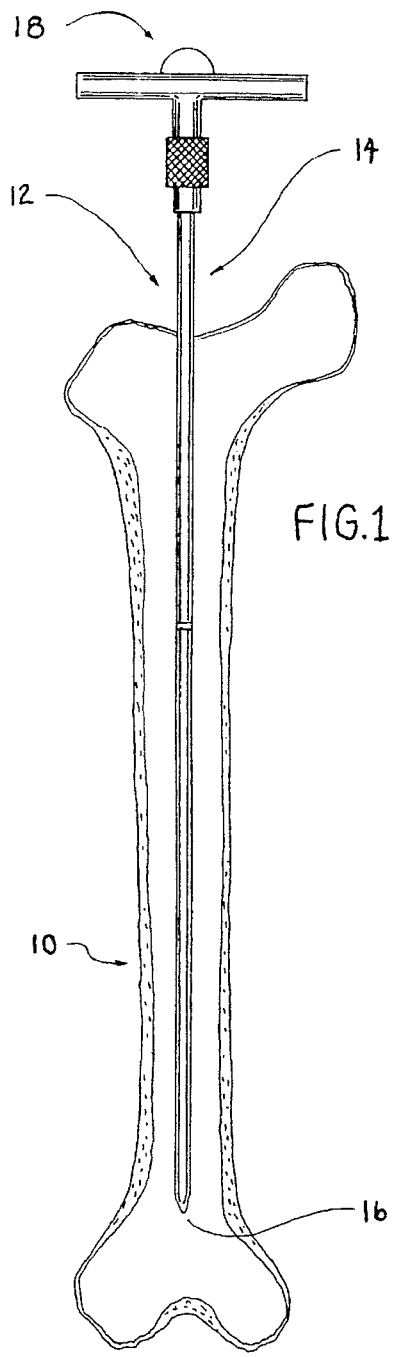
FIG. 1 is a longitudinal cross sectional view of a femur with the centering rod of the present invention inserted into the intermedullary canal of the femur.
Figure 2:
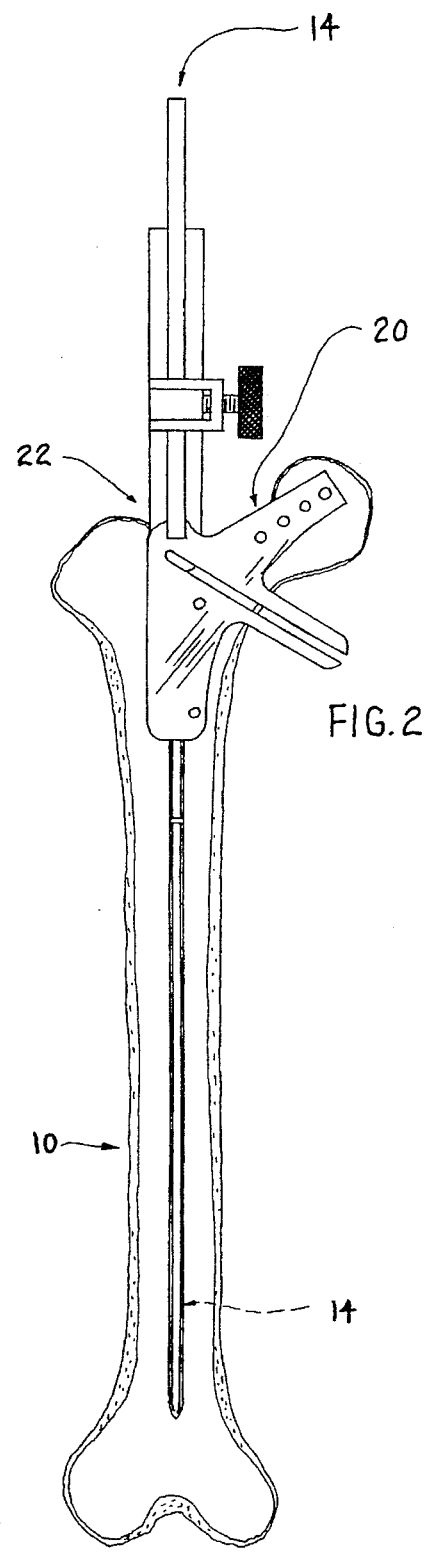
FIG. 2 is a side view of a femur with the centering rod of FIG. 1 shown with dotted lines and further including an osteotomy template having a cannulated securement device telescopically placed over the centering rod.
Figure 3:
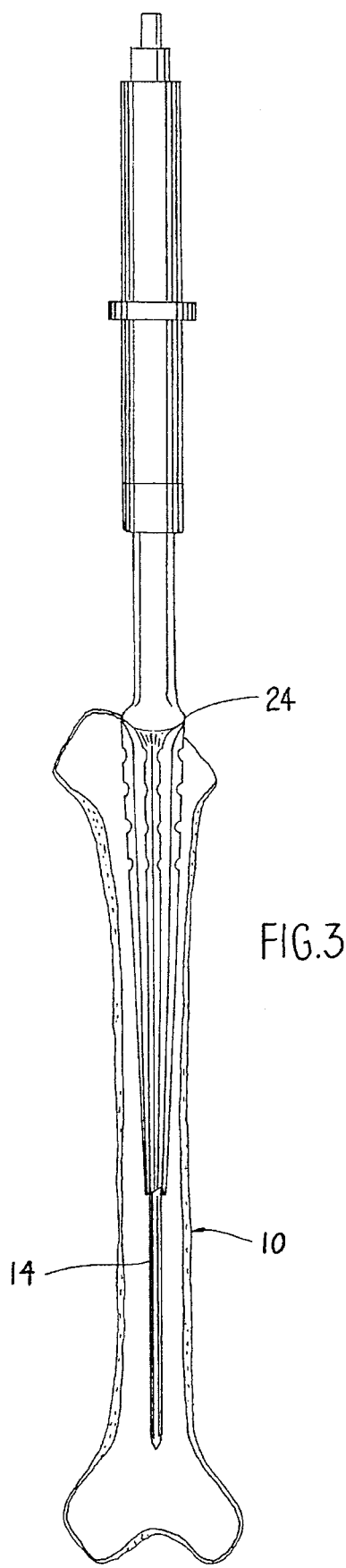
FIG. 3 is a cross sectional view of the femur as shown in FIG. 1 further including a reamer placed over the centering rod (shown with dotted lines) and into the intermedullary canal of the femur.
Figure 4:
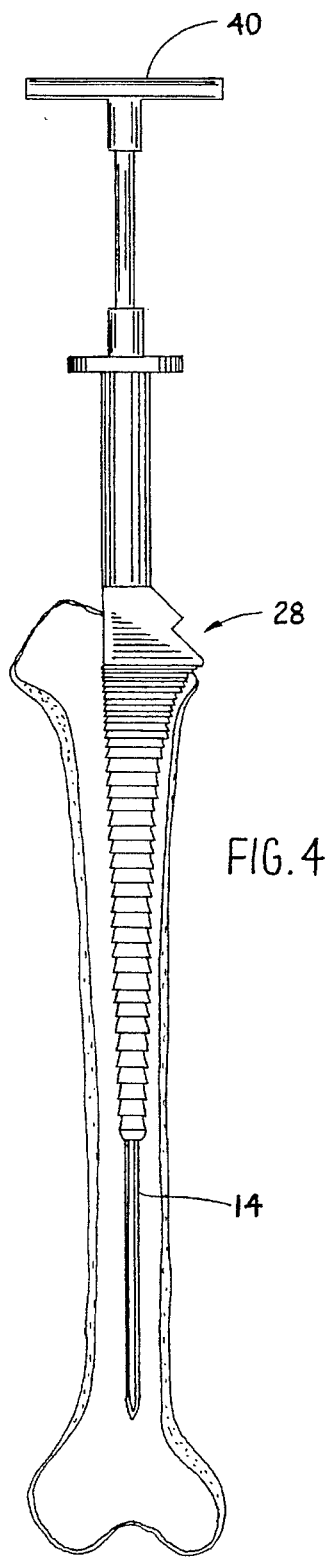
FIG. 4 is a cross sectional view of the femur as shown in FIG. 1 further including a broach telescopically placed over the centering rod (shown with dotted lines) and into the intermedullary canal of the femur.
Figure 5:
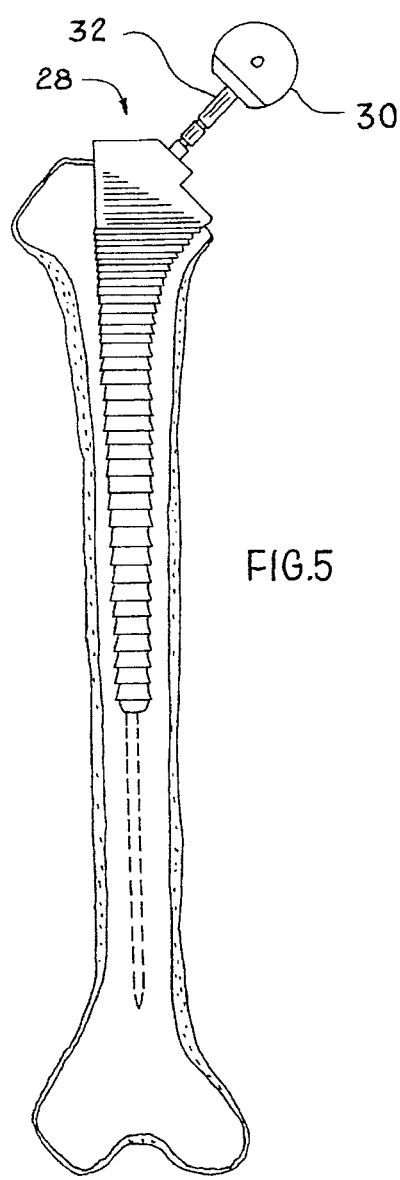
FIG. 5 is the femur as shown in FIG. 1 wherein the centering rod has been removed and a provisional neck is placed on the broach.
Figure 6:
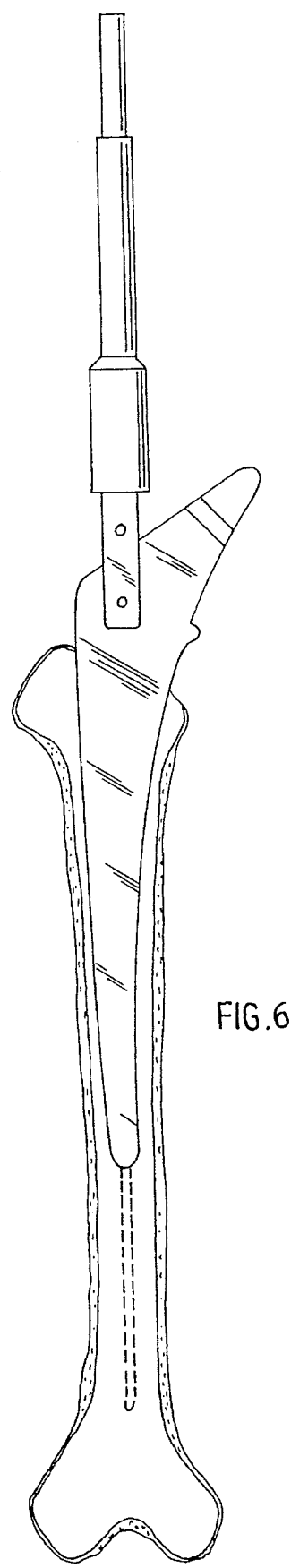
FIG. 6 is a cross sectional view of a femur including a femoral portion of a total hip prosthesis in the intermedullary canal of the femur.

FIG. 1 generally shows a femur 10. A hole is drilled into the proximal portion or first end of the femur at 12. Once the surgeon has drilled into the intermedullary canal at 12, the surgeon then places a substantially rigid centering rod 14 longitudinally into the intermedullary canal of the femur. Preferably, the surgeon continues to insert the centering rod until it becomes embedded in the distal portion or second end of the femur.

As is commonly known in the art, it is very important to find the center of the intermedullary canal of a bone in preparation for receiving a prosthesis. If a prosthesis is not placed into the center of the canal, uniform stress distribution is not achieved.

Although the centering rod 12 is preferably formed of stainless steel, any rigid material commonly used in the art of orthopaedic surgery instrumentation may be employed. The critical feature of the centering rod 12 is that it is rigid for first locating the central axis of the bone and second, to act as a guide for preparation of the intermedullary canal. This is discussed more fully below.

A centering rod 12 used to find the central axis of an intermedullary canal may vary in size depending upon the overall size of the patient's bone. The centering rod 12 ranges in size from about 3 to about 9 millimeters in diameter by about 100 to about 600 millimeters in length. Preferably, the centering rod of the present invention is about 6 millimeters in diameter and about 450 millimeters in length. The centering rod tip is preferably pointed 16 to facilitate placement of the centering rod 12 into the intermedullary canal. The rod tip comprises about 5 degrees to about 45 degrees and preferably about 24 degrees.

As shown in FIG. 1, a handle 18 may be placed at the free end of the centering rod 12. A handle 18 provides a means for the surgeon to insert or impact the rod with a mallet, or remove the rod. Once the rod is placed, the bone is ready for osteotomization or cutting to expose the intermedullary canal for preparation of the canal.

The present invention utilizes an osteotomy guide 20 which includes a rotatable cannulated securement means 22. The surgeon places a cannulated bore of the securement means over the substantially rigid centering rod 14. The centering rod 14 provides a means of accurately orienting the osteotomy cut to the long axis of the bone. This direct orientation of the osteotomy template 20 to the bone axis is a great advancement in orthopaedic surgery. As is commonly known, most bones are not flat and an osteotomy template does not generally rest upon a bone surface without moving or slipping making it difficult to orient the template 20. A cannulated securement device 22 attached to the osteotomy template 20 provides assurance to the surgeon that the osteotomy template 20 does not move until she moves it. It is noted that the centering rod 14 is in place along the entire longitudinal axis of the femur 10 in FIG. 2 and is shown with a dotted line.

Figure 7:
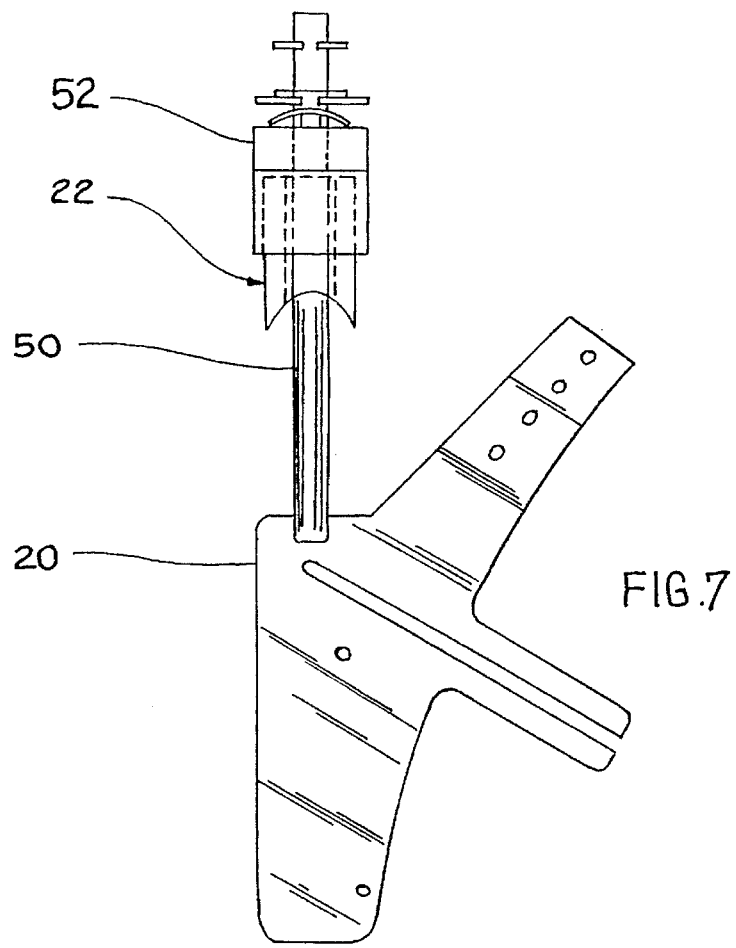
FIG. 7 is a side view of the osteotomy guide of the invention.
Figure 8:
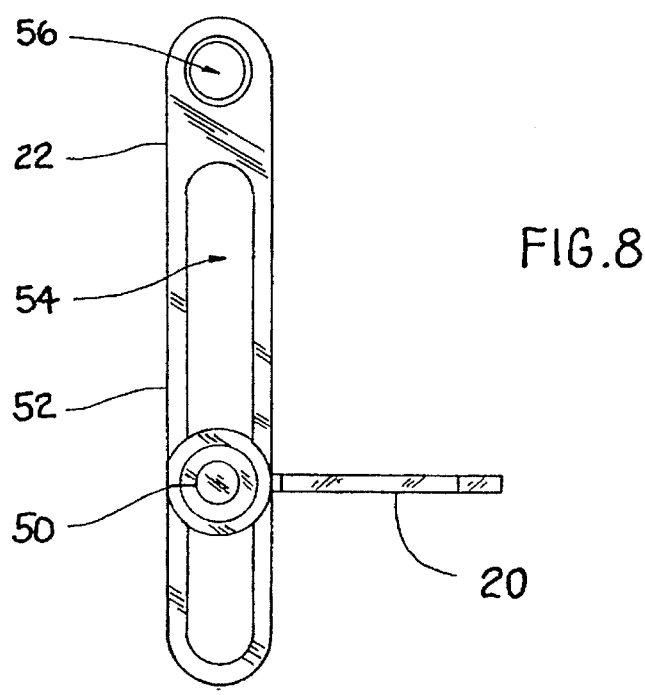
FIG. 8 is a top view of the osteotomy guide shown in FIG. 1.

An osteotomy template 20 with securement device 22 is shown in FIGS. 7 and 8. The osteotomy template 20 of the present invention includes a cannulated securement guide 22 attached to the template 20. Generally, the securing guide 22 is comprised of a rod 50 which extends vertically from the template 20. A sliding actuating guide 52 is placed over the rod 50. The sliding guide 52 contains two apertures therein. The first aperture is an elongated opening 54 which receives rod 50. Rod 50 is allowed to slide inside the length of elongate opening 54. The second aperture in the sliding device 52 is bore 56 which is suited for telescopically receiving the centering rod 14. When bore 56 is placed over centering rod 14, the template 20 is centered along the longitudinal axis of the bone 10. The osteotomy template 20 and rotatable cannulated securement guide 22 ensures that the osteotomy cut is accurately oriented to the long axis of the bone 10. Since only a small portion of the bone is visible during the operating procedure, a surgeon has difficulty locating the center axis of the bone 10 to orient the osteotomy cut. The osteotomy template 20 and rotatable cannulated securement guide 22 is preferably manufactured from stainless steel, although any material commonly known in the art of orthopaedic instruments may be used to form the device.

The intermedullary canal is now exposed and the surgeon proceeds preparing the cavity for a prosthesis. The surgeon telescopically places a substantially rigid cannulated reamer 24 over the centering rod 14. The surgeon then advances and rotates the reamer 24 along the centering rod 14 and into the intermedullary canal of the bone 10. Cartilage and bone is severed from the intermedullary canal region when the surgeon rotates the reamer 24. Once a surgeon believes enough tissue is severed, the surgeon removes the cannulated reamer 24 from the bone and removes the reamer 24 from the centering rod 14.

Figure 9:
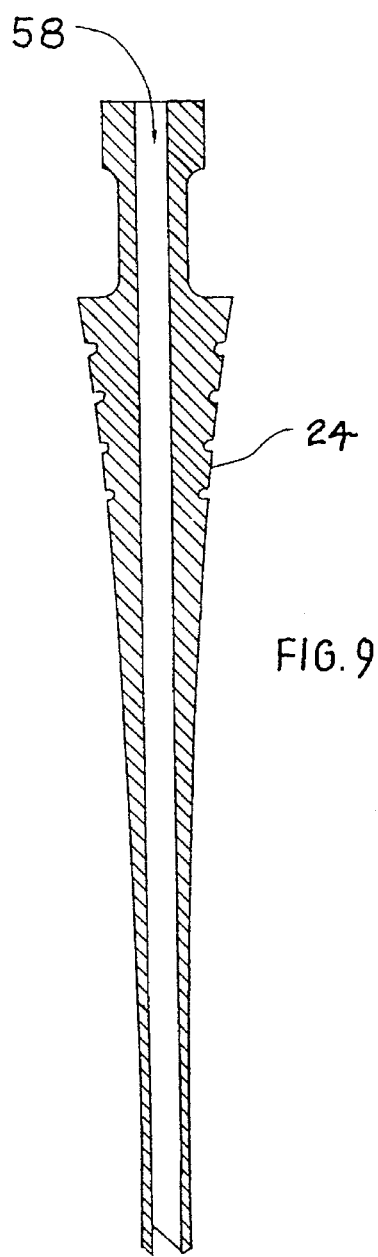
FIG. 9 is a longitudinal cross-sectional view of the reamer of the present invention.
Figure 10:
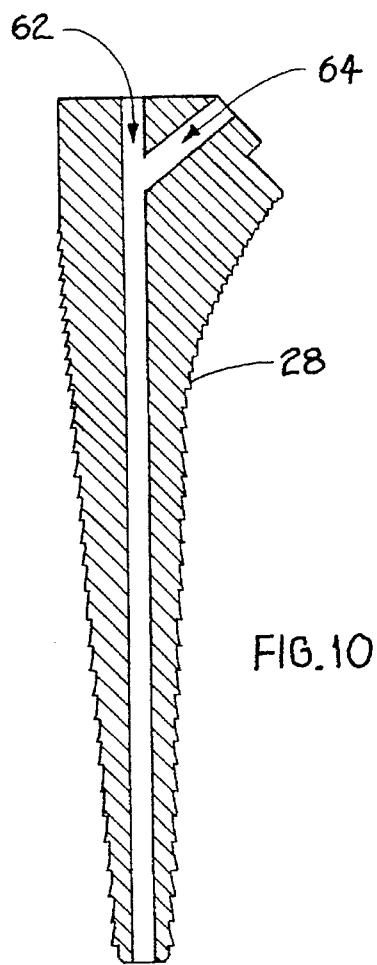
FIG. 10 is a longitudinal cross-sectional view of the broach of the present invention.
Figure 11:
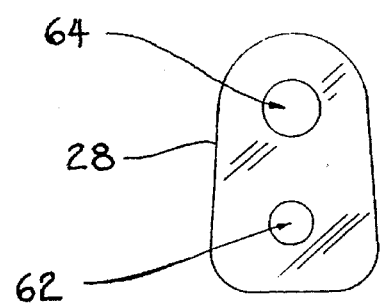
FIG. 11 is a top plan view of the broach of the present invention.
Figure 12:
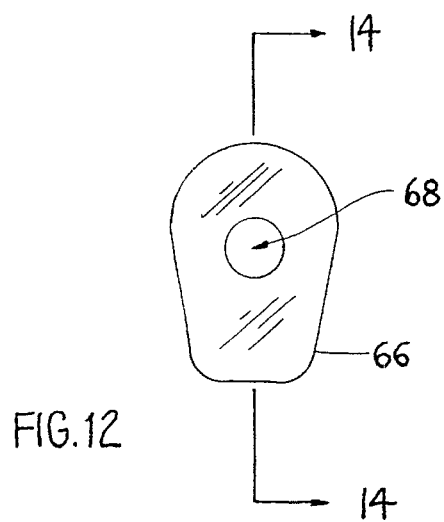
FIG. 12 is a top plan view of the box chisel of the present invention.
Figure 13:
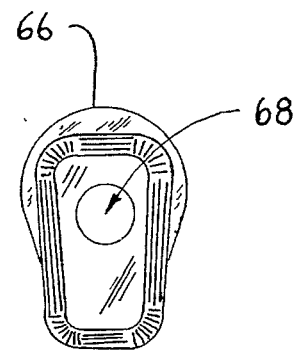
FIG. 13 is a bottom view of the box chisel of the present invention.
Figure 14:
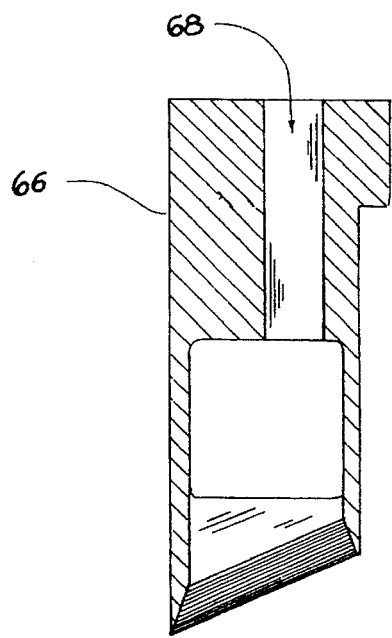
FIG. 14 is a cross-sectional view of the box chisel of the present invention taken along line 14—14.
Figure 15:
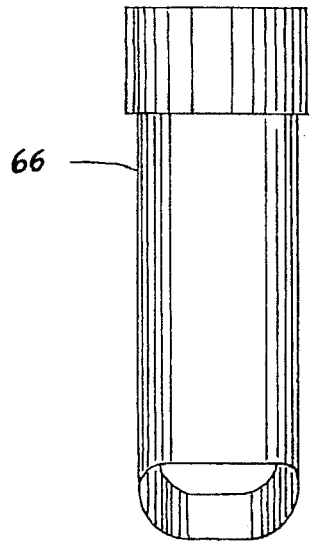
FIG. 15 is a rear view of the box chisel of the present invention.

The reamer 24 of the present invention is similar to those reamers commonly known in the art of orthopaedic surgery having longitudinal flutes extending the length of the tissue-contacting portion of the reamer. As best shown in FIG. 9, the reamer 24 of the invention further includes a longitudinal bore 58 which centrally traverses the length of the reamer 24. The bore 58 extends the length of the reamer 24 to allow the reamer 24 to telescopically receive the centering rod 14. Although a tapered reamer is shown in the Figures, any type of reamer may be prepared and used for the present invention. If, however, the reamer 24 contained an excessively long handle portion, the bore 58 would not necessarily be required to pierce the length of the handle to allow the reamer 24 to function appropriately in the method of the present invention. This is the case for each cannulated instrument described herein. The reamer 24 of the invention is formed of substantially rigid material such as stainless steel, titanium, cobalt chrome, or composites thereof. Preferably, stainless steel is used.

Due to the method of utilizing the centering rod 14, a reamer 24 having a larger diameter and more aggressive fluting 60 thereon can be utilized to sever tissue from the intermedullary canal. Therefore, a larger bore is created in the intermedullary canal of the bone 10 for increased success of placing the broach 28.

By using the centering rod 14, a surgeon is able to control preparation of the intermedullary canal. For instance, the surgeon does not have to worry that the reaming action will not extend along the longitudinal axis of the bone. Therefore, there is less concern with respect to whether or not an excessively large cavity is created which is not suited for receiving and maintaining a prosthesis. Likewise, less concern exists regarding cracking the bone. A surgeon is less likely to jar the reamer outside of the cavity and crack the cancellous or cortical portions of the bone.

After an appropriate amount of tissue is severed, the bone is next ready for broaching. Again, the method of the present invention utilizes a cannulated instrument. A surgeon telescopically places a broach 28 having a central longitudinal bore or cannulation 62 over the centering rod 14. As described with the reamer 24, the longitudinal bore 62 of the broach 28 extends through the length of the broach. The bore 62 of the broach 28 allows the broach to telescopically receive centering rod 14. By placing the broach over centering rod 14 and into the intermedullary canal of the bone, a surgeon is assured of consistently employing the broach along the axis of the centering rod and therefore inserting the broach into the exact same cavity as previously created by the reamer 24. Again, there is less likelihood of cracking the cortical portion of the bone using the instrumentation and method of the present invention.

The broach 28 of the present invention is similar to those known in the art, however, as discussed, the broach includes a longitudinal bore 62. The broach 28 is further formed of any material commonly known in the art of orthopaedic instrumentation, including but not limited to stainless steel, cobalt chrome, or titanium. Preferably, stainless steel is used to make the broach 28 of the invention.

Once the broach 28 is securely in place, the centering rod 14 is removed from both the bone and the broach 28. A provisional neck 30 is then placed into a diagonal bore 64 of the broach 28. A diagonal bore 64 accepts the stem 32 of the provisional neck to achieve proper neck length for a trial reduction. The provisional neck 30 is adjusted to achieve proper range of motion. The broach 28 and provisional neck 30 are now removed from the bone 10. Finally, the cavity is prepared and ready to receive a prosthesis.

Any type of prosthesis may be employed in the present invention including but not limited to a cemented or a press-fit prosthesis.

Optionally, the method of the present invention may include a step with a cannulated box chisel 66. The box chisel 66, as shown in FIGS. 12 through 14 is again cannulated in order to telescopically receive the centering rod 14. The box chisel 66 is inserted over the centering rod 14 and into the intermedullary canal after the reaming step is complete. The box chisel 66 includes a longitudinal bore 68 which extends through the chisel. The box chisel 66 creates a cavity having compatible geometry with that of the prosthesis. That is, the chisel 66 creates an almost rectangular cavity at the proximal end of the femur. Again, the method and instrumentation of the present invention allows the surgeon to chisel the bone without an undue concern of breaking or cracking the cortical portion of the bone. The surgeon is further assured that the chiseled area is in the correct position along the central axis of the bone.

The longitudinal bores in the instrumentation are of a suitable diameter to telescopically receive and advance along a centering rod. The instrumentation bores are preferably of uniform diameter in a particular instrument but may vary in size depending upon the diameter of the centering rod utilized in a particular procedure. The longitudinal bores of the instrumentation are greater than 3 millimeters in diameter and preferably about 7 to about 8 millimeters in diameter. The size of the longitudinal bore is directly correlated to the size of the centering rod utilized which is dictated by the size of the bone being prepared for a prosthesis.

The overall size of the instrumentation of the present invention is also variable. As is commonly known in the art, the size of instruments used during a particular procedure depends upon the size of the bone being prepared for a prosthesis. The present invention anticipates this size variability. Therefore, one can manufacture the cannulated instruments of the present invention in any size suitable for orthopaedic surgery.

In addition to helping the surgeon reduce the chances of cracking the cortical portion of the bone and allowing a surgeon a greater opportunity to place a prosthesis along the central longitudinal axis of a bone, the present method and instrumentation has other advantages over the prior art. The present invention facilitates a more routine surgical procedure. A surgeon is afforded a greater likelihood of successful surgery if the operation proceeds in a routine manner. A routine surgery also reduces time spent conducting the surgery. This reduces both the amount of time that a patient is anesthetized and also reduces the amount of time the operating room is occupied. Operating rooms are exceedingly expensive in today's marketplace and the present invention helps to reduce these health care costs.

The present invention also reduces the likelihood that an excessively large cavity is prepared for the prosthesis. Because the prosthesis is more likely to be placed along the central longitudinal axis of the bone, the patient has more uniform stress distribution when placing his or her weight on the prosthesis. Additionally, routine surgery leads to quicker healing time and allows a patient to ambulate more quickly after surgery.

One skilled in the art will recognize that the details of the previous embodiment may be varied without departing from the spirit and scope of the invention.

We claim:

1. An orthopedic broach apparatus for use on intramedullary cancellous bone and cortical bone, the apparatus comprising:

an asymmetrical main body portion having an outer broaching surface for removing bone and dressing the bone surface, and a longitudinal bore extending the length of said main body; and a centering rod, sufficiently rigid so as to be capable of being driven through intramedullary cancellous bone to become substantially embedded within the intramedullary cancellous bone along a line projecting along the centering rod's longitudinal axis aligned with the central axis of the bone, and having a diameter substantially equivalent to the longitudinal bore diameter so as to be telescopically slidably engageable within the longitudinal bore, wherein the centering rod is positionable in the longitudinal bore for guiding the asymmetrical main body along the centering rod's longitudinal axis.

2. The apparatus of claim 1 in which the longitudinal bore has a diameter of between about 3 and about 9 millimeters.

3. The apparatus of claim 1 in which the asymmetric main body is constructed of one of the materials selected from the group consisting of:

stainless steel, cobalt chrome and titanium.

4. The apparatus of claim 1 in which the asymmetric main body has a proximal end and a distal end with the longitudinal bore extending from the proximal end to the distal end, and further comprising a second bore extending from the proximal end diagonally intersecting the longitudinal bore.

5. The apparatus of claim 1 in which the longitudinal bore has a diameter of about 6 millimeters.

6. The apparatus of claim 1 wherein the centering rod comprises a rigid shaft having a substantially uniform diameter and terminating in a tapered end.

* * * * *